United States Patent
Furchak et al.

(10) Patent No.: US 9,297,047 B2
(45) Date of Patent: Mar. 29, 2016

(54) MOLECULAR BEACON BASED ASSAY FOR THE DETECTION OF BIOMARKERS FOR BREAST CANCER METASTASIS

(71) Applicants: Jennifer Furchak, Kalamazoo, MI (US); Erik Guetschow, Ann Arbor, MI (US); William Alexander Black, Chapel Hill, NC (US)

(72) Inventors: Jennifer Furchak, Kalamazoo, MI (US); Erik Guetschow, Ann Arbor, MI (US); William Alexander Black, Chapel Hill, NC (US)

(*) Notice: Subject to any disclaimer, the term of this patent is extended or adjusted under 35 U.S.C. 154(b) by 41 days.

(21) Appl. No.: 14/353,959

(22) PCT Filed: Oct. 23, 2012

(86) PCT No.: PCT/US2012/061413
§ 371 (c)(1),
(2) Date: Apr. 24, 2014

(87) PCT Pub. No.: WO2013/062931
PCT Pub. Date: May 2, 2013

(65) Prior Publication Data
US 2014/0315207 A1  Oct. 23, 2014

Related U.S. Application Data

(60) Provisional application No. 61/628,100, filed on Oct. 24, 2011.

(51) Int. Cl.
*C12Q 1/68* (2006.01)
*C07H 21/02* (2006.01)
*C07H 21/04* (2006.01)

(52) U.S. Cl.
CPC ............ *C12Q 1/6886* (2013.01); *C12Q 1/6818* (2013.01); *C12Q 2600/158* (2013.01)

(58) Field of Classification Search
None
See application file for complete search history.

(56) References Cited

FOREIGN PATENT DOCUMENTS

WO   WO 2006/034215   3/2006
WO   WO 2006/060561   6/2006

OTHER PUBLICATIONS

Guetschow, et al., Analytical and Bioanalytical Chemisty, vol. 404, No. 2, p. 399-406, Jun. 13, 2012.
International Search Report With Written Opinion for PCT/US2012/061416 of Jan. 15, 2013.
Monroy-Contreras, et al., Journal of Nucleic Acids, vol. 32, No. 6, p. 474-415, Jan. 1, 2011.
Raja, et al., Clinical Chemistry, American Association for Clinical Chemistry, vol. 51, No. 5, p. 862-890, Mar. 3, 2005.

*Primary Examiner* — Carla Myers
(74) *Attorney, Agent, or Firm* — Hueschen and Sage

(57) ABSTRACT

The invention encompasses molecular beacon (MB) probes for monitoring the presence of human breast cancer biomarkers and for the analysis of breast cancer metastasis. The molecular beacon is an oligonucleotide probe which sensitively and specifically identifies biomarker mRNA in samples, in the presence of serum, in minimal time using fluorescence detection. The molecular beacons may be comprised in kits for the detection/quantitation of cancer biomarkers in clinical samples. The invention provides improvements in simplicity, accuracy, and speed over current methods, which could allow for improved patient treatment and prognoses.

9 Claims, 9 Drawing Sheets

Figure 1. The structure of a molecular beacon. The MB has a stem-loop structure, with regions in grey complementary to the mRNA. When the MB is in a closed state, the fluorophore and quencher are in close proximity, reducing fluorescence. The secondary structure of PIP mRNA in the binding region is shown with regions complementary to the MB shown in grey. When the MB and mRNA form a stable duplex, the fluorophore and quencher are remote from one another, resulting in a fluorescent signal.

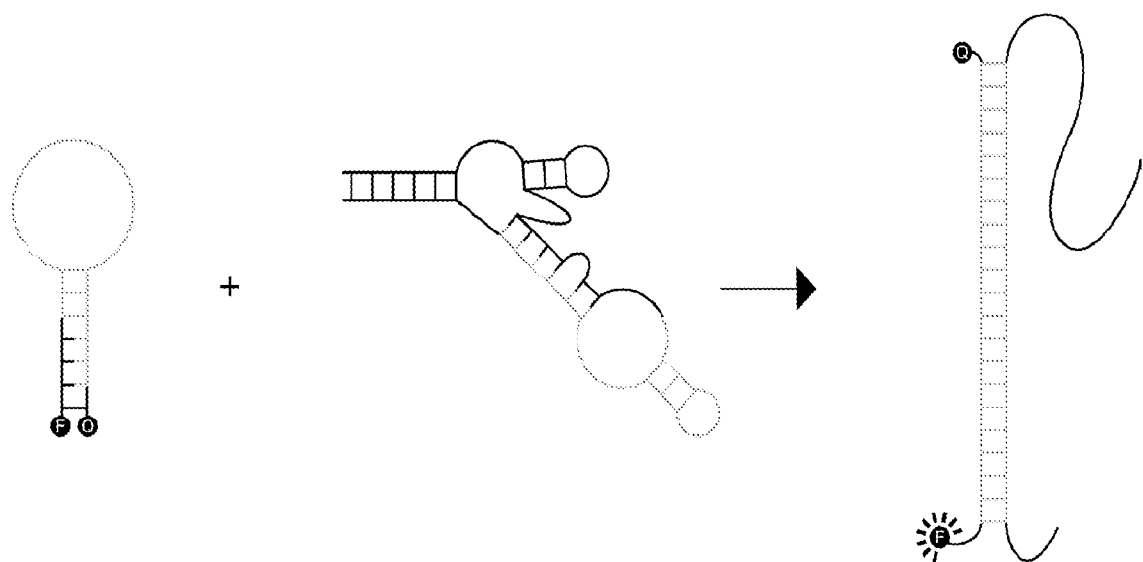

Figure 2. PIP mRNA in MB binding region (SEQ ID NO. 4). Eight bases were removed from the labeled bulge (*) in the native full-length PIP mRNA sequence to make the secondary structure construct for increased transcriptional efficiency. Two nonsense nucleotides (GG [in *italics*]) were added at the 5' end of PIP mRNA (SEQ ID NO. 4) for transcriptional efficiency. Grey bases indicate complementarity between the MB and mRNA.

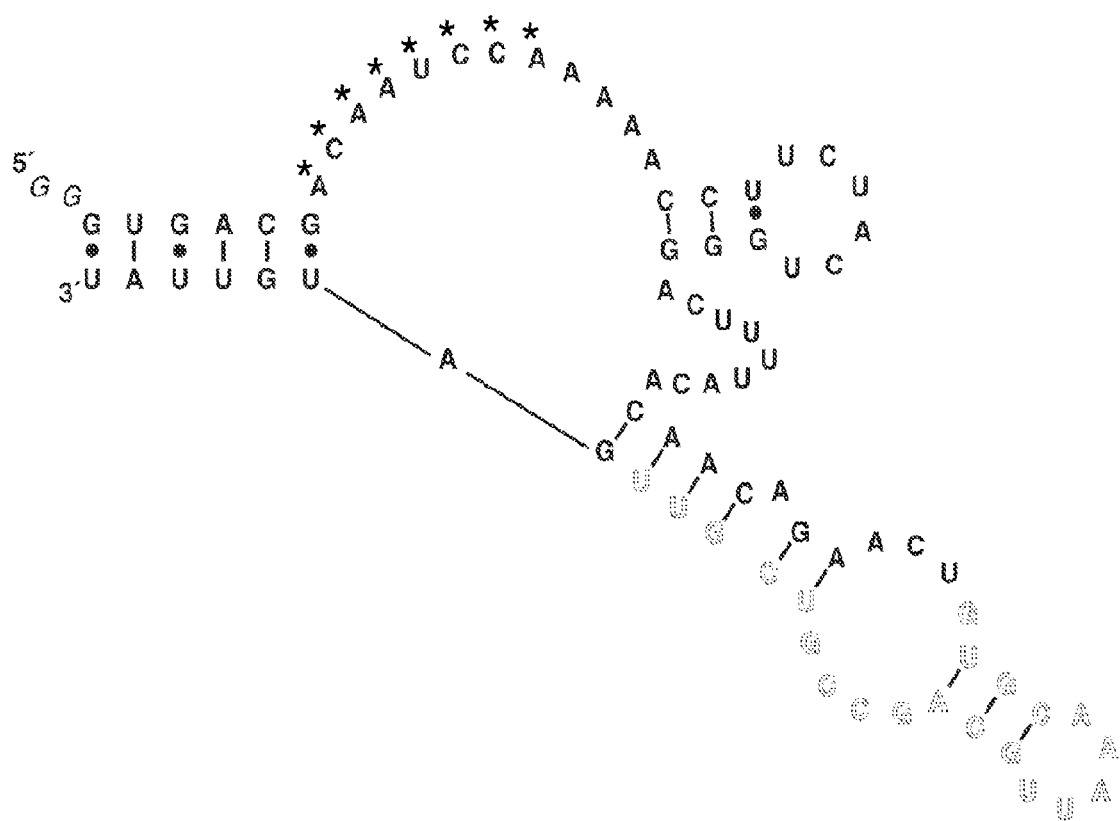

Figure 3. Hybridization of the PIP molecular beacon to PIP mRNA over time.
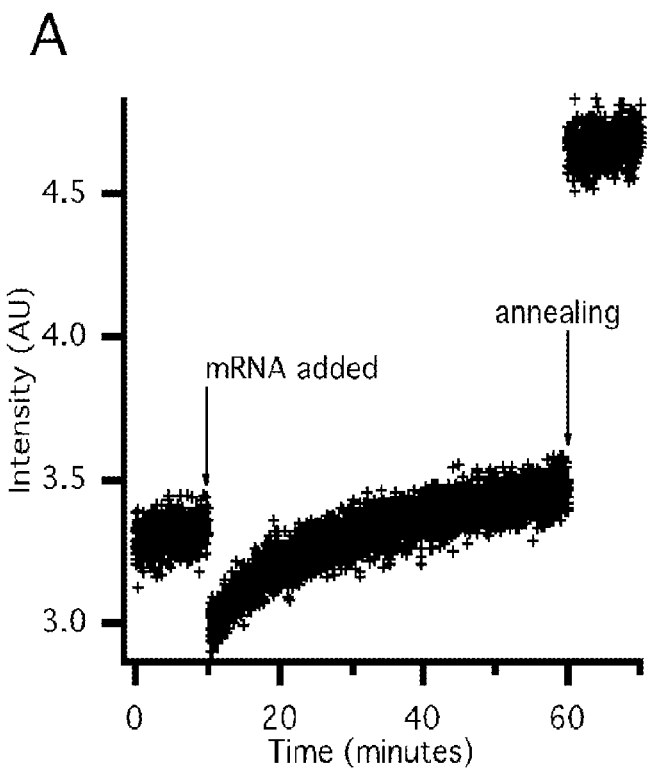
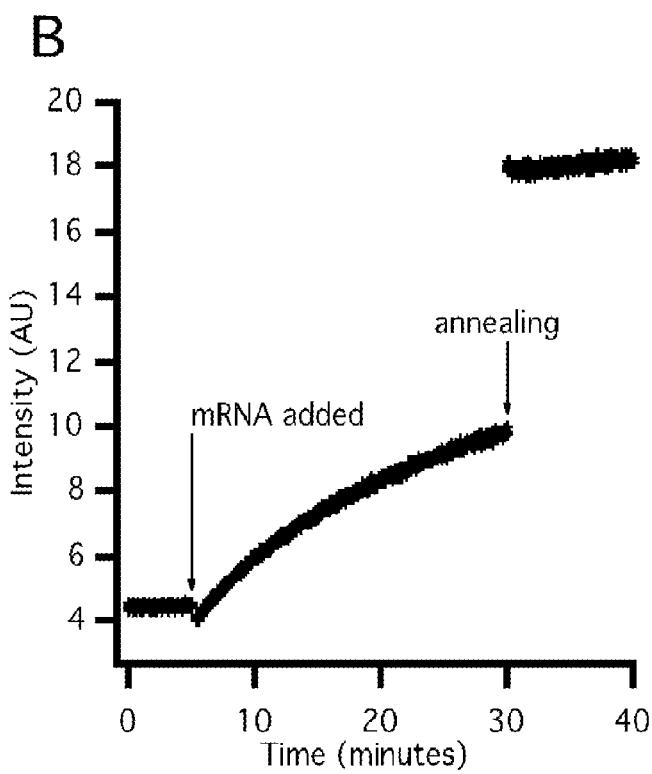

Figure 4. Response of the MB to PIP mRNA over a range of concentrations up to 20 nM (n=3).
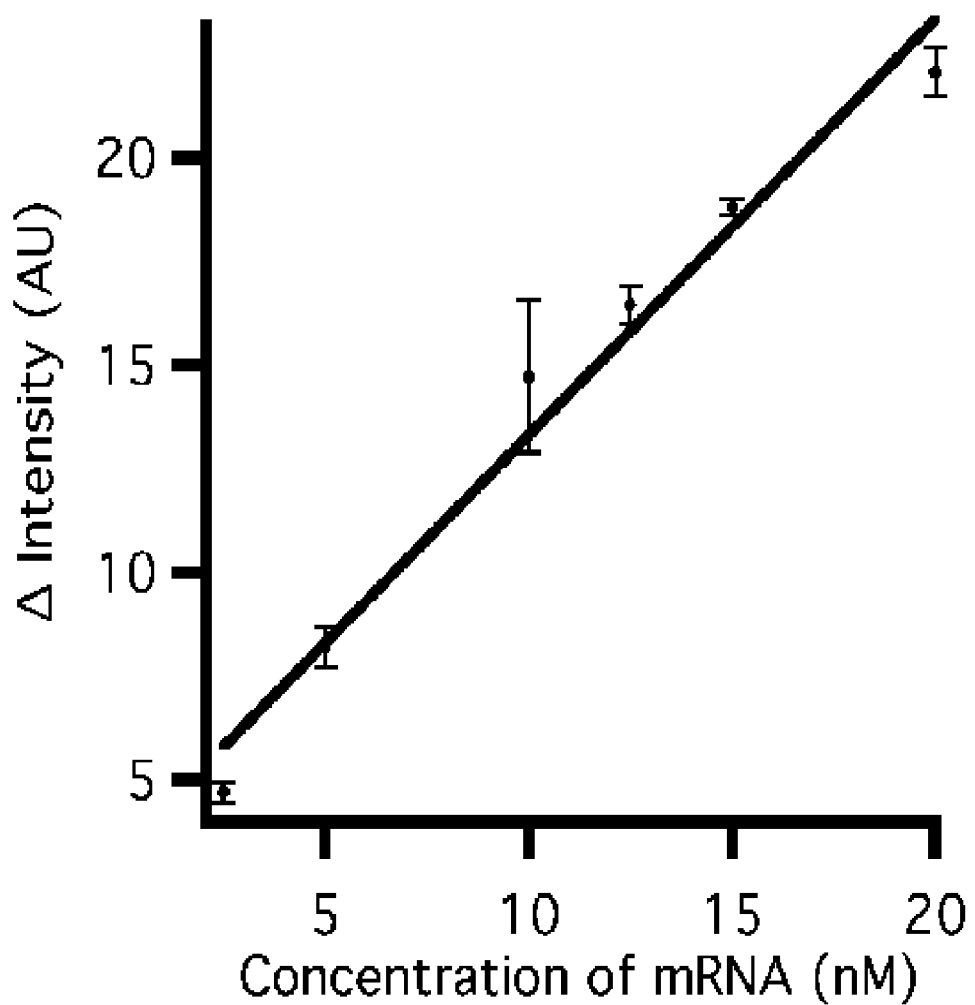

Figure 5. Comparison of the response of PIP MB to full-length PIP mRNA and PIP mRNA construct over the concentration range of 2.5 pM to 2.5 nM.
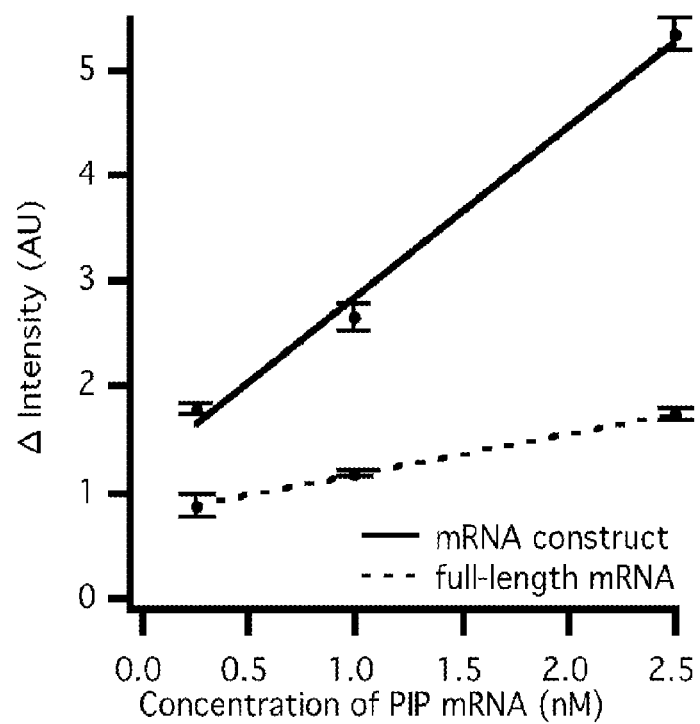

Figure 6. The response of the PIP molecular beacon to PIP mRNA over a range of concentrations.
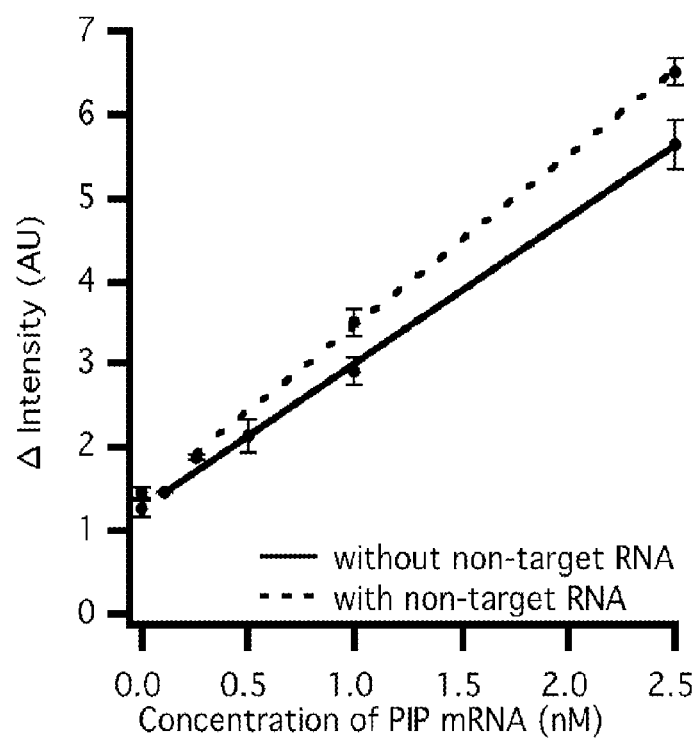

Figure 7. The response of the PIP molecular beacon to varying concentrations of PIP mRNA in buffered samples and undiluted serum samples.
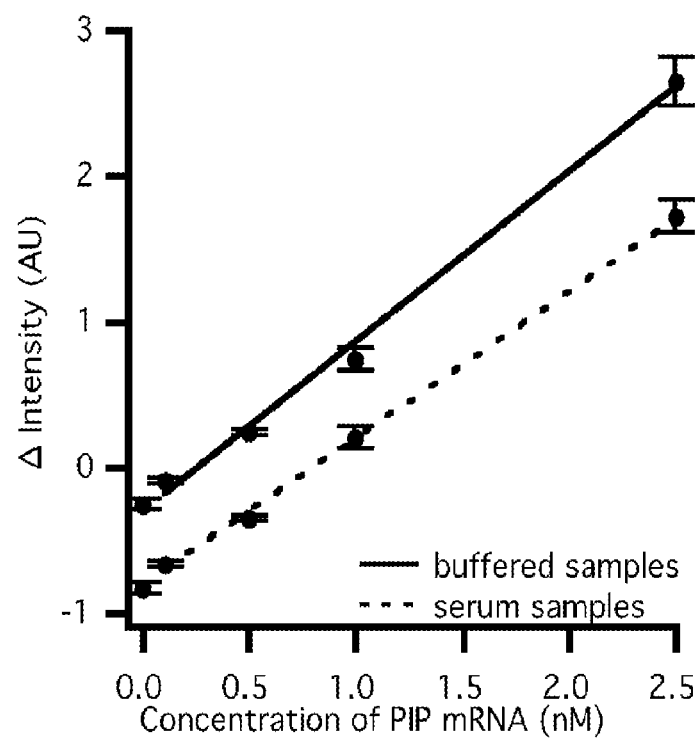

Figure 8. Hybridization of MB to HER2 mRNA over time. HER2 mRNA added to MB at 5 min, resulting in a decrease in fluorescence intensity due to dilution of the sample followed by a gradual increase as MB binds mRNA. A dramatic increase results after annealing at 30 min.
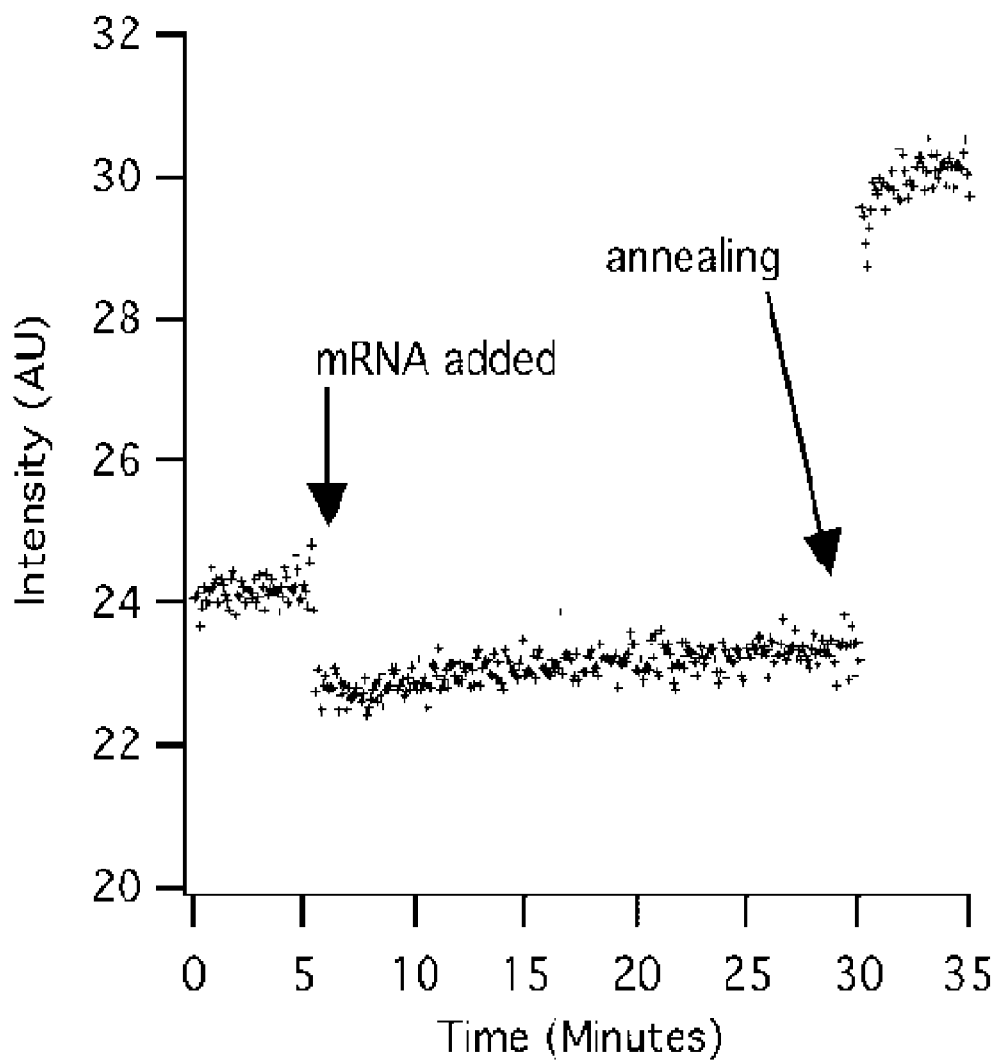

Figure 9. The response of the MB to HER2 mRNA over a range of concentrations showing the reproducibility, sensitivity, and specificity of the assay. The LOD is 3.8 nM and R2 value is 0.996 (n 0 3).
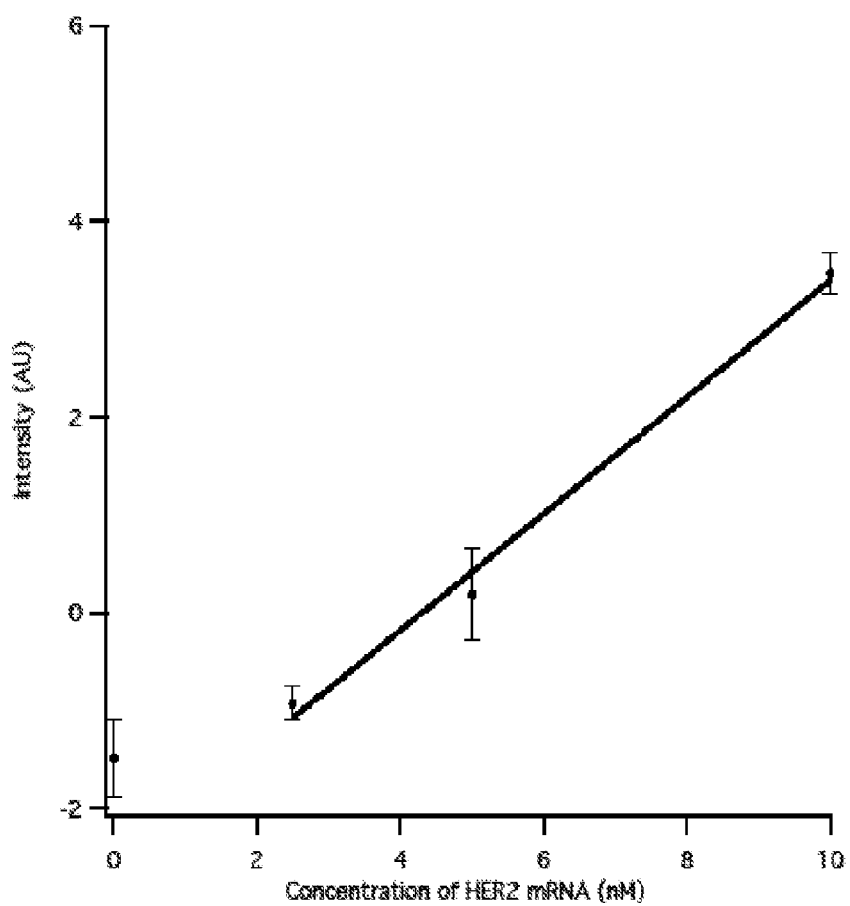

MOLECULAR BEACON BASED ASSAY FOR THE DETECTION OF BIOMARKERS FOR BREAST CANCER METASTASIS

BACKGROUND OF THE INVENTION

Breast cancer is a prevalent form of cancer among women in the United States. The detection, removal, and treatment of breast carcinoma are important focuses of the medical and scientific community. A combination of better surgical techniques for removal of tumors, improved treatment options, and earlier detection of cancer has lead to a decline in cancer mortality over the last two decades. Mortality is increasingly linked to early, undetected metastatic cancer.

Traditionally, analysis of disease progression and metastasis is achieved through physical tumor staging parameters, such as tumor size and presence of nodal or distal metastases, using the tumor-node-metastases staging system. This method is qualitative, changes with advances in diagnosis, and requires a large pool of data (i.e. more patients) to provide accurate results. An analytical detection method would be advantageous for detection of metastatic breast cancer and accurate quantitation of circulating tumor cells throughout treatment to develop patient-specific treatment options and would represent a significant improvement over traditional methodologies for analyzing disease progression and metastasis.

Clinical trials have demonstrated that detection of specific biomarkers for differentiation of normal and circulating tumor cells in peripheral blood serum, bone marrow, or lymph node samples allows for the identification of breast cancer metastasis. Of these, serum sampling is a relatively painless technique that allows for frequent sampling. Monitoring levels of breast cancer biomarkers such as carcinoembryonic antigen (CEA), cancer antigen 15-3(CA15-3), prolactin inducible protein (PIP); mammaglobin (hMAM); and human epidermal growth factor receptor 2 (HER2), as either mRNA or protein has been demonstrated as effective for detecting breast cancer metastasis. Furthermore, the search for additional biomarkers continues. Biomarkers potentially offer a variety of information about metastatic cancer; for example, PIP is involved in cell division and tumor proliferation, hMAM is nearly breast tissue specific and overexpressed in breast cancer, and HER2 is a cell membrane tyrosine kinase growth factor receptor that is associated with poor prognosis when overexpressed. Therefore, their detection has potential power in detecting metastasis, characterizing circulating tumor cells, understanding disease progression, and designing treatment.

In clinical diagnostic applications, the total amount of target nucleic acid in a sample is often very low. In order to overcome the limitations in detecting small levels of mRNA, schemes for target amplification have been developed. The most widely used target amplification technique is reverse transcription-polymerase chain reaction (RT-PCR).

Current technology for the detection of biomarker mRNA uses RT-PCR. This method relies on reverse transcription of mRNA biomarkers to DNA followed by amplification through polymerase chain reaction to a detectable level. The results of amplification may be separated by gel electrophoresis and visualized by ethidium bromide staining, or the nucleic acid amplification may be detected by real-time analysis to determine the presence of breast cancer biomarkers.

Conventional detection is accomplished through detection of cancer cells in lymph tissue by staining of tissue sections embedded in paraffin wax with haematoxylin and eosin dyes. This method cannot detect low numbers of tumor cells. Other methods based on antibody binding, such as immunohistochemistry that utilizes labeled antibodies to bind and detect cancer cells, have been developed to more sensitively stain sectioned lymph node tissue. This method is time consuming and requires trained scientists for analysis. Antibody based detection methods include ELISA, fluorescence microscopy, immunocytochemistry, and flow cytometry, which take advantage of antibody specificity to target tumor cells for detection. Methods based on nucleic acids include PCR detection of free DNA, RT-PCR detection of free mRNA, and fluorescence in situ hybridization (FISH) for detection of gene amplifications. FISH utilizes fluorescent molecular probes that detect the presence of specific DNA sequences within the cellular or nuclear environment to monitor the upregulation of specific genes during metastasis.

Commonly the detection of protein biomarkers in serum is achieved through the use of ELISA. Briefly, ELISA requires the use of an immobilized primary antibody, which binds the biomarker protein of interest, and a secondary antibody, which also binds the biomarker protein in a sandwich assay that results in a signal dependent on target concentration. This method can be performed in a 96-well plate allowing for high sample-throughput after sample preparation is complete. However, it is costly and time consuming due to the use of multiple antibodies and washing steps in analysis.

Current detection of mRNA biomarkers most commonly relies on reverse transcription-polymerase chain reaction (RT-PCR), which has been demonstrated as effective for detecting micrometastasis in clinical samples of serum and lymph nodes. This method requires reverse transcription of messenger RNA biomarkers to DNA followed by amplification through PCR to a detectable level. The results of amplification are then separated by agarose gel electrophoresis and visualized by ethidium bromide staining or detected by real-time analysis to determine the presence of breast cancer biomarkers.

RT-PCR holds promise for the detection of circulating tumor cells through the use of mRNA biomarkers. This method of detection is rudimentarily quantitative and, therefore, superior to conventional methods, such as the TNM staging method, for detection of metastasized cancer. The low limit of detection associated with RT-PCR as a result of amplification allows for improved detection, which is expected to lead to improved prognosis and greater treatment options. Additionally, the influence of gene sequencing and analysis has made the procedure for PCR and RT-PCR quite common and the technology for it exists in labs across the country. Finally, RT-PCR can be performed with many samples in parallel allowing for the analysis of multiple samples from the same individual or single samples from multiple individuals for rapid screening.

The molecular beacons of the invention may be used in conjunction with RT-PCR to probe the reaction products and identify the presence of PIP, HER2 and/or hMAM mRNA present in a clinical sample. RT-PCR reaction products may be probed with the molecular beacons of the invention to detect the presence of PIP, HER2 and/or hMAM amplified cDNAs. Moreover, real-time measurement of amplification products may be conducted by including the molecular beacons of the invention in the RT-PCR reaction mixture. Analysis may be conducted according to methods known to those skilled in the art.

Previous research has demonstrated that monitoring multiple biomarkers simultaneously improves the accuracy of detection of breast cancer metastasis. Gene panels of two or more biomarkers increase efficiency of cancer cell detection, reduce the number of false positive and negative results, and provide more information about the metastasized cancer. Multiplex assays using combinations of the molecular beacons of the invention, can detect several targets simultaneously having spectrally resolved fluorescent probes. The PIP, HER2 and hMAM MBs could be used in a panel for multiplexed detection for fast and accurate quantitative detection and monitoring of breast cancer metastasis.

Even in light of several advantages, RT-PCR has a few significant disadvantages in terms of analysis time, efficiency, and accuracy. RT-PCR begins after total RNA extraction from blood, a process that takes at least two days (ABI Prism Nucleic Acid preparation, Applied Biosystems, Grand Island, N.Y., USA). The total time for RT-PCR is typically 5 hours or more including temperature cycling, gel preparation, running the gel, and visualization. The process is too time consuming for rapid analysis in hospital or clinical settings. Separation and visualization by slab gel electrophoresis and ethidium bromide staining has limited ability for quantitation, which is crucial to developing patient-specific treatment regimens. To compound the issues further, there are difficulties in multiplex analysis. Analysis of three or more biomarkers proves difficult due to unequal amplification of the sequences due to sample conditions, extracellular serum factors, and the formation of primer-dimers resulting in false-positive and false-negative results.

Some of the shortcomings of RT-PCR have been addressed with the development of quantitative reverse-transcription polymerase chain reaction (Q-RT-PCR), which undergoes all the same steps as RT-PCR with the addition of quantification after each round. This is achieved through the use of a target specific molecular beacon (MB) or intercalating dye, which fluoresces upon hybridization with target DNA. Q-RT-PCR, therefore, improves quantification in RT-PCR but brings its own disadvantages to the analysis. The measurement of expression, based on the DNA amplification, using Q-RT-PCR is generally accepted to be reliable, but the steps leading up to the measurement have varying degrees of reliability and reproducibility. Replication of the cell culture, RNA extraction, and reverse transcription steps is necessary to increase accuracy quantification of Q-RT-PCR, but also significantly increases sample analysis time.

RT-PCR holds promise for the detection of circulating tumor cells as it is semi-quantitative and, therefore, offers advantages over conventional methods. Even in light of these advantages, there is a need to provide sensitive and accurate detection of tumor biomarkers without the use of RT-PCR.

The instant molecular beacons may be used for probing clinical samples detecting the presence of biomarker mRNA by methods known to those skilled in the art. Such methods include, for example, fluorescence in situ hybridization (FISH), wherein the molecular beacons of the invention are hybridized to mRNA of whole cells or tissue samples followed by fluorescence analysis of the molecular beacon on the cells and/or tissue using fluorescence microscopy. Clinical samples, for example, fixed and permeablized whole cells or biopsy tissues, bodily fluids, and lysates of whole cells or biopsy tissues, which have been contacted with the molecular beacons of the invention may be analyzed for the presence of biomarker mRNA using, for example, flow cytometric detection.

Ideally, an analytical approach would allow for accurate, sensitive, and specific identification of biomarkers directly in samples containing serum, in minimal time and with a straightforward and cost-effective procedure.

The use of molecular beacons (MBs) may provide a clinical detection method that offers advantages over RT-PCR. MBs are single-stranded DNA molecules that are designed with a region complementary to the target oligonucleotide (the loop) flanked by self-complementary regions at the 5' and 3' ends (the stem), which hybridize to form a stem-loop structure. The ends terminate in a fluorophore and quencher pair. In the absence of target oligonucleotides, the fluorophore and quencher are in close proximity resulting in resonance energy transfer between the fluorophore and quencher and minimal fluorescence emission. Upon formation of a stable duplex with the target molecule, the fluorophore is remote from the quencher resulting in an increased fluorescent signal. Since their development, MBs have been used in many bioanalytical applications for their specificity and sensitivity for target nucleic acids.

Herein, the development of a product for the sensitive and specific detection of PIP mRNA, HER2 mRNA and hMAM mRNA using MBs is described. The assay for biomarker mRNA detection is fast, simple, and inexpensive, and can detect mRNA in the presence of serum, showing potential for use in biomarker detection for breast cancer metastasis.

BRIEF SUMMARY OF THE INVENTION

Molecular beacons for the detection of biomarkers of breast cancer metastasis have been developed. The molecular beacons, in the form of modified oligonucleotides, hybridize to PIP, HER2 or hMAM biomarker mRNA thereby providing a means to detect and/or quantify the levels of biomarker mRNA.

The molecular beacons of the invention may be described as an oligonucleotide probe consisting essentially of the sequence set forth in SEQ ID NO. 6, wherein the 5' nucleotide of the probe is labeled with at least one fluorophore and the 3' nucleotide of the probe is labeled with at least one quencher, such an oligonucleotide probe, wherein the sequence set forth in SEQ ID NO. 6 exhibits a nucleotide sequence which is complementary to human prolactin inducible protein (PIP) mRNA, such an oligonucleotide probe, wherein the at least one fluorophore is tetrachloro-6-carboxyfluorescein, such an oligonucleotide probe, wherein the at least one quencher is BLACK HOLE QUENCHER® 1 (Black Hole Quencher (BHQ) dye having a quenching wavelength range of 480-580 nm), such an oligonucleotide probe, wherein the first six nucleotides of an oligonucleotide having the sequence set forth in SEQ ID NO. 6 are complementary to the last six nucleotides of the oligonucleotide having the sequence set forth in SEQ ID NO. 6, such an oligonucleotide probe, which is in a form of a stem-loop structure wherein the at least one fluorophore is in proximity to the at least one quencher whereby fluorescence of the at least one fluorophore is quenched by the at least one quencher, such a kit comprising the oligonucleotide probe and a positive control PIP mRNA consisting of the sequence set forth in SEQ ID NO. 5, such an oligonucleotide probe consisting essentially of the sequence set forth in SEQ ID NO. 8, wherein the 5' nucleotide of the probe is labeled with at least one fluorophore and the 3' nucleotide of the probe is labeled with at least one quencher, such an oligonucleotide probe, wherein the sequence set forth in SEQ ID NO. 8 exhibits a nucleotide sequence which is complementary to human epidermal growth factor receptor 2 (HER2) mRNA, such an oligonucleotide probe, wherein the at least one fluorophore is TEXAS RED® (a bright red-fluorescent dye having a maximum excitation of 596 nm and a maximum emission at 615 nm), such an oligonucleotide probe, wherein the at least one quencher is BLACK HOLE QUENCHER® 2 (Black Hole Quencher (BHQ) dye having a quenching wavelength range of 550-650 nm), such a method of detecting the presence of PIP mRNA in a subject having been diagnosed with cancer comprising contacting a bodily fluid and/or tissue biopsy from the subject with the oligonucleotide probe under conditions which allow hybridization of the oligonucleotide probe to the PIP mRNA in the bodily fluid and/or tissue biopsy and comparing a detected signal to a control, such a method wherein the oligonucleotide probe and the PIP mRNA are contacted in the presence of serum.

In an embodiment, products comprising the molecular beacons are contemplated. The product may be in the form of a kit for determining the presence of and/or the levels of expression of PIP mRNA, HER2 mRNA and/or hMAM mRNA, biomarkers for breast cancer metastasis, the kit comprising a molecular beacon. The assay for determining the presence of and/or the levels of biomarker mRNA expression is sensitive and reproducible with a limit of detection in the pM range. In the presence of non-target mRNA, the assay shows similar sensitivity, indicating that the PIP molecular beacon is specific to its target mRNA. The robustness of the assay is demonstrated by the similar limit of detection and sensitivity in undiluted serum samples.

Total analysis time for the MB assay is significantly shorter than protocols based on RT-PCR. A single sample in buffer can be analyzed in 15 minutes compared to at least 5 hours in RT-PCR. The decrease in total analysis time is even more significant if the sample is present in a complex matrix. The assay can be preformed directly in undiluted serum, eliminating the need for days of sample preparation.

With a limit of detection in the picomolar range, the assay does not compare with current protocols based on RT-PCR in terms of detection limit. RT-PCR relies on amplification to increase concentration of mRNA in serum to a detectable level and therefore is able to detect very low concentrations. However, the absence of an amplification step the instant method decreases the possibility of false positive and negative results.

Strategies for improving the detection of biomarker mRNA include preconcentrating the mRNA or tumor cells with a fast and efficient procedure before detection with a molecular beacon.

The potential impact of this work in detection and understanding of breast cancer metastasis lies in improvements in simplicity, accuracy, and speed over current methods. This dramatically reduces the total time for sample analysis from days to hours. The ability to sensitively and specifically detect biomarkers directly in serum samples, as well as in biopsy material, in minimal time and with a straightforward procedure could allow for improved patient treatment and prognoses. Ultimately, simplification of biomarker detection will allow higher sample throughput, resulting in better understanding of disease progression.

BRIEF DESCRIPTION OF THE FIGURES

FIG. 1. The structure of a molecular beacon. The MB has a stem-loop structure, with regions in grey complementary to the mRNA. When the MB is in a closed state, the fluorophore and quencher are in close proximity, reducing fluorescence. The secondary structure of PIP mRNA in the binding region is shown with regions complementary to the MB shown in grey. When the MB and mRNA form a stable duplex, the fluorophore and quencher are remote from one another, resulting in a fluorescent signal.

FIG. 2. PIP mRNA in MB binding region (SEQ ID NO. 4). Eight bases were removed from the labeled bulge (*) in the native full-length PIP mRNA sequence to make the secondary structure construct for increased transcriptional efficiency. Two nonsense nucleotides (GG in italics) were added at the 5' end of PIP mRNA (SEQ ID NO. 4) for transcriptional efficiency. Grey bases indicate complementarity between the MB and mRNA.

FIG. 3. Hybridization of MB to PIP mRNA over time. (A) Full-length PIP mRNA added to MB at 10 minutes resulting in a gradual increase in fluorescence due to binding. PIP mRNA and MB were heat denatured and cooled to anneal at 60 minutes, resulting in a dramatic increase in fluorescence intensity as they form a stable duplex. (B) Shorter secondary structure PIP mRNA (SEQ ID NO. 5) added to MB at 5 minutes, resulting in an increase in fluorescence intensity due to binding follow by a dramatic increase after annealing at 30 minutes. The MB binds to both constructs, though less effectively to the full-length mRNA, likely due to intermolecular interactions within the full-length mRNA that are not accounted for in the secondary structure construct.

FIG. 4. Response of the MB to PIP mRNA over a range of concentrations up to 20 nM (n=3).

FIG. 5. Comparison of the response of PIP MB to full-length PIP mRNA and PIP mRNA secondary-structure construct over the concentration range of 2.5 pM to 2.5 nM. The dashed line represents the full-length PIP mRNA and the solid line represents the shorter secondary structure mRNA construct for PIP mRNA (SEQ ID NO.5). The assay is more sensitive to the shorter mRNA than to the full-length mRNA as indicated by the difference in slopes.

FIG. 6. The response of the MB to PIP mRNA over a range of concentrations showing the reproducibility, sensitivity, and specificity of the assay. The solid line represents the assay performed in the absence of non-target mRNA with an LOD of 167 pM and $R^2$-value of 0.9996 (n=3). The dashed line indicates the assay performed in the presence of non-target mRNA with an LOD of 141 pM and $R^2$-value of 0.9995 (n=3).

FIG. 7. The response of PIP MB to varying concentrations of PIP mRNA in buffered samples and undiluted serum samples showing the robustness of the assay in a complex matrix. The dashed line represents undiluted serum samples and the solid line represents buffered samples. For buffered samples, the $R^2$ value is 0.9970 and the LOD is 144 pM (n=3). For undiluted serum samples, the $R^2$ value is 0.9993 and the LOD is 57 pM (n=3).

FIG. 8. Hybridization of MB to HER2 mRNA over time. HER2 mRNA added to MB at 5 min, resulting in a decrease in fluorescence intensity due to dilution of the sample followed by a gradual increase as MB binds mRNA. A dramatic increase results after annealing at 30 min.

FIG. 9. The response of the MB to HER2 mRNA over a range of concentrations showing the reproducibility, sensitivity, and specificity of the assay. The LOD is 3.8 nM and R2 value is 0.996 (n 0 3).

DETAILED DESCRIPTION OF THE INVENTION

Prolactin inducible protein (PIP) is a secreted protein that is over-expressed in breast carcinoma and thought to have a role in tumor proliferation and metastasis. PIP mRNA has been used for detection of breast cancer metastasis using RT-PCR. A molecular beacon specific for PIP mRNA was designed for the simple detection of breast cancer metastasis. The mRNA sequence for PIP mRNA (NCBI AccessionNM_002652) was determined using GenBank entries and a literature reference.

The MB has a stem-loop structure with a suitable donor fluorophore and acceptor quencher pair. Suitable donor fluorophores for use in molecular beacons are known to those skilled in the art. Moreover, quencher moieties of a donor-acceptor pair are also known to those skilled in the art.

The PIP MB has a stem-loop structure is modified to include a tetrachloro-6-carboxyfluorescein on the 5' end and BLACK HOLE QUENCHER® 1 (Biosearch Technologies, Inc., Novato, Calif.) on the 3' end. BLACK HOLE QUENCHER® 1 quenches tetrachloro-6-carboxyfluorescein emission when the stem is base-paired ("closed") and the two moieties are in close proximity. The bases in the loop of the MB and some of the bases in the stem are complementary to PIP mRNA (see FIG. 1). The MB sequence is complementary to the region of conserved secondary structure and incorporates nucleotides at the 5' and 3' ends which are self-complementary, thereby forming a closed, stem-loop structure.

A PIP MB DNA, 5'-TGTGCAACGACGGCTG-CAATTTGCACA-3' (SEQ ID NO. 6), was chemically synthesized and modified to incorporate a fluorophore and a quencher at the 5' and 3' ends, respectively. When the MB binds PIP mRNA, the base-pairing of the stem is disrupted (the MB is "open"), and the quencher and fluorophore are no longer sufficiently close to produce quenching. This results in fluorescence emission. The designed MB is complementary to the PIP mRNA bases indicated in FIG. 2.

To confirm MB-mRNA hybridization, PIP mRNA was spiked into a sample containing MB in buffer and the resulting fluorescence emission was monitored over time. FIG. 3 illustrates that the MB binds PIP mRNA resulting in an increase in fluorescence intensity. The initial fluorescence intensity of the MB is low as the stem is closed and fluorophore and quencher are in close proximity (FIG. 3A). After mRNA is added, there is a decrease in fluorescence intensity due to dilution of the sample followed by a gradual increase in fluorescence intensity, indicating that MB and mRNA molecules form a stable duplex that causes spatial separation of the fluorophore and quencher. The nucleic acids in the sample are then heat denatured and annealed by slowly cooling the sample. After annealing, the fluorescence intensity increases dramatically as more MB and mRNA duplexes are formed.

PIP mRNA is too long (564 bases) to synthesize by chemical methods, so a shorter mRNA fragment that was predicted with energy minimization by mfold to have locally conserved secondary structure in the MB binding region (bases 292 through 379 in the full-length sequence, FIG. 2) was designed. Eight (8) bases were excluded from the mRNA fragment, which bases were not predicted to be involved in base-pairing interactions (marked with stars in FIG. 2), and are expected to have no effect on the mRNA conformation. This secondary-structure construct having the sequence set forth in SEQ ID NO. 2 was synthesized to be a target mRNA for the PIP MB and was used as a surrogate target to represent the full-length, native PIP mRNA. The secondary-structure construct forms all of the hydrogen bonds expected to require disruption for MB binding and consists of only 87 bases and, thus, can be chemically synthesized as DNA and transcribed to RNA.

To test the validity of the secondary-structure construct of SEQ ID NO. 2 as a surrogate for the full-length mRNA, the binding of the MB to the secondary-structure construct target was compared to the MB binding to the full-length mRNA target. As with the full-length mRNA (FIG. 3A), the initial fluorescence intensity of the MB alone is low, the fluorescence intensity increases gradually after mRNA is added, and the fluorescence intensity increases dramatically after annealing the MB and mRNA (FIG. 3B). This indicates that the MB binds to both constructs. It is noted that the full-length mRNA opens the MB less effectively than the shorter construct, which is evidenced by the slower increase in fluorescence intensity upon addition of mRNA as well as the smaller overall change in intensity from fully closed to fully open MB (FIG. 3A). This difference is likely due to intermolecular interactions within the full-length mRNA that are not accounted for in the secondary structure construct.

An assay for PIP mRNA was developed in which the measured response is the difference in fluorescence intensity of the fully closed MB before mRNA is added from the fully open MB after annealing with mRNA (FIG. 4). Both the secondary-structure construct of SEQ ID NO. 2 (FIG. 5, solid line) and the full-length mRNA (FIG. 5, dashed line) produce concentration dependent responses from the MB over a range in RNA concentration from 250 pM to 2.5 nM. The difference in binding efficiency of the MB to the full-length structure compared to the shorter construct ultimately results in a less sensitive assay (about 4 fold) for the full-length mRNA compared to the secondary structure construct, shown by the smaller slope of the calibration.

Given the difference in slopes of the calibration curves in FIG. 5, it was investigated whether a correction factor could account for the difference in response and reliably predict the concentration of a sample of full-length mRNA when the shorter construct is used for calibration. Using a calibration curve made with secondary structure mRNA and a conversion factor of 0.33 based on the linear regressions to account for difference in secondary structure versus full-length calibration curves, a sample of containing 1.50 nM full-length mRNA had a measured concentration of 1.66 nM, which is approximately 10% error in the concentration. These data demonstrate that the secondary structure construct is a good model for the full-length mRNA and that the secondary construct mRNA may substitute for the full-length mRNA in the analysis of PIP MB binding.

In the assay, the MB response to PIP mRNA increases linearly, reproducibly (RSD below 10%), and with sufficient sensitivity to distinguish a range of concentrations up to at least 2.5 nM, with a limit of detection of 167 pM (FIG. 6, solid line). The addition of non-target RNA to the sample resulted in a similar response, with good reproducibility (RSD below 5%) and a similar sensitivity evidenced by the slope, indicating the specificity of the PIP MB for PIP mRNA (FIG. 6, dashed line). The limit of detection is also similar at 141 pM. In addition to being highly sensitive, the total time for the assay is just a few hours.

The molecular beacon design may help account for the low limit of detection and sensitivity of the assay. PIP mRNA is complementary to the MB loop region as well as part of the stem (FIG. 1). Complementarity in the stem is predicted to increase affinity between the MB and target relative to the affinity of the MB self-complementarity as MBs with target-complementary stems have been shown to form more stable duplexes with target molecules than loop-only MBs.

To evaluate the robustness of the assay, measurements of PIP mRNA directly in serum were made. Because heat denaturing nucleic acids also denatures serum proteins rendering them insoluble, a modified assay which measures change in intensity without heating the sample was developed. The MB was incubated for 3 hours directly in PIP mRNA-spiked serum. For comparison, the modified assay was also performed in mRNA-spiked assay buffer. A similar sensitivity and reproducibility (below 10% RSD for all but one data point) in buffered samples as in serum samples, with no need to clean or prepare the serum before analysis (FIG. 7, solid is buffer and dashed is serum) was observed. The LODs were comparable with 144 pM for buffered samples and 57 pM for undiluted serum samples. This significantly reduces analysis time over other methods to just a few hours by eliminating the need for sample cleaning before analysis.

In an embodiment, the instant invention encompasses a method of detecting and quantifying the amount of PIP mRNA in a sample, wherein the sample may comprise serum, the method comprising the steps of contacting a sample which may contain PIP mRNA with a PIP molecular beacon under conditions which allow binding of the molecular beacon to the PIP mRNA, measuring the amount of fluorescence in the sample, measuring the amount of fluorescence in a control sample which has a PIP molecular beacon but does not comprise PIP mRNA, and calculating the difference in the amount of fluorescence in the test and control samples. An increase in the fluorescence intensity of the test sample over the fluorescence intensity of the control sample means that PIP mRNA is present in the sample.

In an embodiment, the PIP molecular beacon of the invention consists essentially of the sequence set forth in SEQ ID NO. 6, wherein the 5' nucleotide of the sequence set forth in SEQ ID NO. 6 is labeled with at least one fluorophore and the 3' nucleotide of the sequence set forth in SEQ ID NO. 6 is labeled with at least one quencher.

The language "consisting essentially of" means that in addition to those components which are mandatory, other components may also be present in compositions, provided that the essential, basic and/or novel characteristics of the compositions are not materially affected by their presence.

In a further embodiment, the invention encompasses kits which comprise the PIP molecular beacon and a positive control nucleic acid, wherein the sequence of the positive control nucleic acid is set forth in SEQ ID NO.5.

In another embodiment, a molecular beacon for HER2 mRNA, with excitation and emission maxima at 599 nm and 615 nm, respectively, is designed. HER2 is a cell membrane receptor tyrosine kinase involved in signal transduction pathways that lead to growth and differentiation. Over-expression of HER2 can be associated with tumor proliferation and metastasis.

The pre-mRNA for HER2 is alternatively spliced into three splice variants so the molecular beacon was designed to be complementary to a structural motif present in the bases conserved among the splice variants. The HER2 molecular beacon comprising the sequence 5'-TGCCACCAGTTCAG-CAGGTCCGTGGCA-3' (SEQ ID NO. 8) was chemically synthesized and modified to incorporate a TEXAS REDO fluorophore and a BLACK HOLE QUENCHER® 2 at the 5' and 3' ends, respectively.

A secondary structure construct was designed to represent the binding region of the full-length HER2 mRNA. The full-length HER2 mRNA is 4,624 bases and the secondary structure construct represents bases 2,651 through 2,724 in the full-length sequence (NCBI Accession Nos. M12036, NM_004448, and NM_001005862 in GenBank) wherein two nucleotides (GG) were added for transcriptional efficiency. The nucleotide sequence of the HER2 mRNA secondary structure construct is 5'-GGUGCCUCUUAGACCAUGUC-CGGGAAAACCGCGGACGCCUGGGCUCCCAGGAC CUGCUGAACUGGUGUAUGCAGAU-3' (SEQ ID NO. 9).

A MB for hMAM may be designed to be complementary to a region of hMAM mRNA. hMAM mRNA is highly breast specific, though recent studies have found expression in ovary, uterus, cervix, and skin tissues. hMAM is up-regulated in the majority of breast carcinomas. The hMAM molecular beacon is expected to provide concentration-dependent, sensitive, specific responses to hMAM mRNA.

Reference may now be made to various embodiments of the invention as set forth in the examples and illustrated in the attached figures.

EXAMPLES

Example 1

Preparation of Human PIP cDNA and Human PIP mRNA

All nucleic acids were purified by polyacrylamide gel electrophoresis (PAGE) before use. Nucleic acids were denatured at 70° C. for 2 minutes, mixed 2:1 with loading dye (8 M urea; 20 mM EDTA; 5 mM Tris-HCl, pH 7.5; 0.5% w/v xylene cyanol; and 0.5% w/v bromophenol blue), and separated on 20 percent polyacrylamide gels (24 g urea; 25 mL 40% polyacrylamide; 10 mL 5×TBE) at 17 W per gel for approximately 3 hours. DNA was visualized with UV shadowing (100-280 nm). RNA was visualized by ethidium bromide staining of a thin, vertical strip of gel. DNA and unstained RNA were extracted by cutting bands from the gels, crushing, and tumbling over night in water. This process was performed twice and the eluate from both extractions was combined. Extracts were purified by chloroform extraction (24:1 chloroform: isoamyl alcohol solution saturated with TE buffer) and ethanol precipitation. Purified products were reconstituted in 50 µL of sterile water and quantified using UV absorbance at 260 nm.

The full-length PIP cDNA was amplified from a transfection-ready circular plasmid (SC118489, Origene Technologies, Inc., Rockville, Md.) using DNA primers designed to amplify the full sequence of PIP mRNA according to GenBank (forward primer: 5'-CACATTGCCTTCTGTTTTCTC-3' (SEQ ID NO. 1), reverse primer: 5'-AAGCATGTTAA-GAAGTTTATTTTATAG-3' (SEQ ID NO. 2)).

PCR mixtures were prepared to final concentrations of 1×PCR buffer, 200 µM each NTP, 1.5 mM MgCl$_2$, 200 nM forward and reverse primers, 0.02 U/µL NovaTaq™ DNA polymerase, and varying concentrations of template cDNA. For the amplification of PIP cDNA from the circular plasmid, the PCR conditions were 94° C. for 4 min; 20 cycles of 94° C. for 1 min, 59° C. for 1 min (decreased by 0.5° C. per cycle), and 72° C. for 1 min; 30 cycles of 94° C. for 1 min, 49° C. for 1 min, and 72° C. for 1 min; and 72° C. for 10 min.

After amplification, a T7 promoter was added to the full-length sequence by PCR (above) to facilitate transcription of PIP mRNA (forward primer: 5'-CAGTAATACGACTCAC-TATAGGCACATTGCCTTCTGTTTTCTC-3' (SEQ ID NO. 3)). For the addition of the T7 promoter, the PCR conditions were 94° C. for 4 min; 20 cycles of 94° C. for 1 min, 57° C. for 1 min (decreased by 0.5° C. per cycle), and 72° C. for 1 min; 30 cycles of 94° C. for 1 min, 47° C. for 1 min, and 72° C. for 1 min; and 72° C. for 10 min.

RNA was transcribed from a double-stranded DNA template which encoded a T7 promoter upstream of the nucleic acids to be transcribed into mRNA. Solutions for transcription of PIP mRNA were prepared to final concentrations of 200 nM forward and reverse primers, 1.25 U/µL T7 RNA polymerase, T7 polymerase transcription buffer (120 mM HEPES-KOH, pH 7.5; 30 mM $MgCl_2$; 2 mM Spermidine; 40 mM DTT; 0.01% TRITON x-100), 2 mM each NTP, 0.005 U/μL pyrophosphatase (New England Biolabs, Ipswich, Mass.), and 8% PEG. The primers, transcription buffer, and sterile water were mixed and heated to 70° C. for 2 minutes, and nucleic acids allowed to anneal into stable conformations at room temperature before additional reagents were added. The solution was incubated at 37° C. overnight.

A shorter PIP mRNA which was predicted with energy minimization by mfold to have locally conserved secondary structure in the MB binding region (bases 292 through 379 in the full-length PIP sequence) was designed. Eight (8) bases were excluded from the native PIP mRNA in the region, which bases were not predicted to be involved in base-pairing interactions and are expected to have no effect on the mRNA conformation (see FIG. 2). This secondary-structure PIP mRNA construct substitutes for the full-length PIP mRNA in binding assays and exhibits the sequence 5'-GGGUGAC-GAAAACCUUCUACUGGGACUUUUACA-CAACAGAACUGUGCAAAUUGC AGCCGUCG-UUGAUGUUAU-3' (SEQ ID NO. 5). It forms all of the hydrogen bonds expected to require disruption for MB binding and consists of only 87 bases and, thus, can be chemically synthesized as DNA and transcribed to RNA.

Example 2

Preparation of a PIP Molecular Beacon

A PIP MB was designed based on the mRNA sequence for PIP mRNA (NCBI Accession NM_002652) which was determined using GenBank entries and a literature reference. Expected mRNA secondary structures were modeled using mfold energy minimization and a region of secondary structure that was conserved in the majority of possible structures was found. The MB sequence is complementary to the region of conserved secondary structure and incorporates nucleotides at the 5' and 3' ends which are self-complementary, thereby forming a closed, stem-loop structure. A PIP MB DNA, 5'-TGTGCAACGACGGCTGCAATTTGCACA-3' (SEQ ID NO. 6), was chemically synthesized and modified to incorporate a fluorophore and a quencher at the 5' and 3' ends, respectively. A PIP MB of the invention consists essentially of tetrachloro-6-carboxyfluorescein-TGTGCAACGACGGCT-GCAATTTGCACA (SEQ ID NO. 6)-BLACK HOLE QUENCHER® 1.

Example 3

Analysis of the Binding of the PIP Molecular Beacon to PIP mRNA

Samples were prepared to give final concentrations of 50 mM HEPES, pH 7.5; 100 mM $MgCl_2$; 200 mM KCl; 25 mM DTT; 20 nM MB. All solutions were heated to 95° C. for 2 minutes and allowed to anneal at room temperature prior to analysis. Fluorescence emission was monitored with excitation at 521+/−5 nm and emission at 535+/−5 nm at 25° C. using a Cary Eclipse fluorescence spectrophotometer (Agilent Technologies, Inc., Santa Clara, Calif.).

For temporal analysis of MB-mRNA hybridization, each MB sample was spiked with mRNA after establishing a fluorescence baseline. Fluorescence emission was then monitored for 30-60 minutes before the samples were heated to 95° C. for 2 minutes and annealed at room temperature. Emission was monitored for 10 minutes after annealing.

To evaluate the in vitro MB binding to mRNA, the baseline fluorescence intensity was established, target mRNA was then added, the nucleic acids were annealed, and the fluorescence emission was monitored to establish a maximum intensity. All samples were analyzed in triplicate.

The response of the MB to target mRNA was monitored as a function of the change in fluorescence from baseline to maximum intensity. The change in fluorescence intensity was determined by averaging the baseline and maximum fluorescence values over 1 minute and calculating the difference. Values from the triplicate analysis were averaged and standard deviation was determined for error. Analysis of raw data for average fluorescence intensities and standard deviations was performed in Microsoft Excel (Redmond, Wash.) while plotting and curve fitting was performed using IGOR Pro 6 (Lake Oswego, Oreg.).

Hybridization of MB to PIP mRNA over time is shown in FIG. 3. Full-length PIP mRNA was added to MB at 10 minutes resulted in a gradual increase in fluorescence due to binding. PIP mRNA and MB were heat denatured and cooled to anneal at 60 minutes, resulting in a dramatic increase in fluorescence intensity as they form a stable duplex, see FIG. 3A.

Shorter secondary structure PIP mRNA (SEQ ID NO. 5) was added to MB at 5 minutes, resulting in an increase in fluorescence intensity due to binding follow by a dramatic increase after annealing at 30 minutes, see FIG. 3B. The MB binds to both constructs, though less effectively to the full-length mRNA, likely due to intermolecular interactions within the full-length mRNA that are not accounted for in the secondary structure construct.

The response of the MB to PIP mRNA over a range of concentrations up to 20 nM (n=3) is shown in FIG. 4.

A comparison of the response of PIP MB to full-length PIP mRNA and PIP mRNA secondary-structure construct over the concentration range of 2.5 pM to 2.5 nM is shown in FIG. 5. The dashed line represents the full-length PIP mRNA and the solid line represents the shorter secondary structure mRNA construct for PIP mRNA (SEQ ID NO.5). The assay is more sensitive to the shorter mRNA than to the full-length mRNA as indicated by the difference in slopes.

Non-target RNA was used in assays to determine the specificity of a PIP MB for the target PIP mRNA construct. 10 nM non-target mRNA (5'-GCGACCCUGAUGAGCCCUGC-GAUGCAGAAAGGUGCUGACGACACAUCGAAACG GU-3' (SEQ ID NO. 7)) was added to all samples comprising target PIP mRNA and binding was evaluated.

The response of the PIP MB to target PIP mRNA in the presence of non-target RNA was monitored as a function of the change in fluorescence from baseline to maximum intensity. The change in fluorescence intensity was determined by averaging the baseline and maximum fluorescence values over 1 minute and calculating the difference. Values from the triplicate analysis were averaged and standard deviation was determined for error. Analysis of raw data for average fluorescence intensities and standard deviations was performed in Microsoft Excel (Redmond, Wash.) while plotting and curve fitting was performed using IGOR Pro 6 (Lake Oswego, Oreg.).

The response of the MB to PIP mRNA over a range of concentrations showing the reproducibility, sensitivity, and specificity of the assay is shown in FIG. 6. The solid line represents the assay performed in the absence of non-target mRNA with an LOD of 167 pM and $R^2$-value of 0.9996 (n=3). The dashed line indicates the assay performed in the presence of non-target mRNA with an LOD of 141 pM and $R^2$-value of 0.9995 (n=3).

Example 4

Undiluted Serum MB Assay

The in vitro MB binding assay as in Example 3 was repeated for analysis of PIP MB response to target PIP mRNA in complex samples in the presence of undiluted bovine serum. All solutions were heated and annealed prior to the addition of bovine serum. Baseline fluorescence intensity was established for 1 minute and then PIP mRNA was added. The samples were incubated in a 25° C. water bath for 3 hours at which point maximum fluorescence intensity was measured.

The response of the PIP MB to target PIP mRNA was monitored as a function of the change in fluorescence from baseline to maximum intensity. The change in fluorescence intensity was determined by averaging the baseline and maximum fluorescence values over 1 minute and calculating the difference. Values from the triplicate analysis were averaged and standard deviation was determined for error. Analysis of raw data for average fluorescence intensities and standard deviations was performed in Microsoft Excel (Redmond, Wash.) while plotting and curve fitting was performed using IGOR Pro 6 (Lake Oswego, Oreg.).

The response of PIP MB to varying concentrations of PIP mRNA in buffered samples and undiluted serum samples showing the robustness of the assay in a complex matrix is shown in FIG. 7. The dashed line represents undiluted serum samples and the solid line represents buffered samples. For buffered samples, the $R^2$ value is 0.9970 and the LOD is 144 pM (n=3). For undiluted serum samples, the $R^2$ value is 0.9993 and the LOD is 57 pM (n=3). The similar sensitivities and LODs in serum samples compared with buffered samples suggest that the MB is sufficiently specific for application to PIP mRNA detection directly in serum samples.

Example 5

The Use of Molecular Beacons in Conjunction with RT-PCR for the Detection/Quantification of Biomarker mRNA Breast tissue samples of a subject suspected as having breast cancer or tumors of a subject diagnosed with cancer are excised from the subject and the mRNA is extracted from the tissue and/or tumor samples. The mRNA is subjected to RT-PCR using standard techniques known to those skilled in the art using forward and reverse primers specific for human PIP, for example, the primers of SEQ ID NO. 1 and SEQ ID NO. 2. After several cycles of amplification, the PIP cDNA is contacted with PIP molecular beacons and the amount of fluorescence in the sample is quantified and compared to RT-PCR amplified negative control samples (i.e., do not contain PIP mRNA).

Breast tissue samples of a subject suspected as having breast cancer or tumors of a subject diagnosed with cancer are excised from the subject and the mRNA is extracted from the tissue and/or tumor samples. The mRNA is subjected to RT-PCR using standard techniques known to those skilled in the art using forward and reverse primers specific for human HER2. After several cycles of amplification, the HER2 cDNA is contacted with HER2 molecular beacons and the amount of fluorescence in the sample is quantified and compared to RT-PCR amplified negative control samples (i.e., do not contain HER2 mRNA).

Breast tissue samples of a subject suspected as having breast cancer or tumors of a subject diagnosed with cancer are excised from the subject and the mRNA is extracted from the tissue and/or tumor samples. The mRNA is subjected to RT-PCR using standard techniques known to those skilled in the art using forward and reverse primers specific for human hMAM. After several cycles of amplification, the hMAM cDNA is contacted with hMAM molecular beacons and the amount of fluorescence in the sample is quantified and compared to RT-PCR amplified negative control samples (i.e., do not contain hMAM mRNA).

Blood samples from a subject suspected as having breast cancer or blood samples from of a subject diagnosed with cancer are drawn for analysis. The mRNA is obtained from the blood or blood products of the subjects and is amplified by RT-PCR and quantified as above.

Example 6

Analysis of Biopsy Material

Biopsy material from, for example, a lymph node or a tissue, is excised from a subject and prepared according to methods known to those skilled in the art. The biopsy material is fixed and/or permeablized and incubated with a PIP, HER2 and/or hMAM molecular beacon. The fluorescence of the biopsy material is observed using fluorescence microscopy and/or flow cytometric detection. The molecular beacons are observed to selectively bind markers in the biopsy material.

Example 7

Detection of PIP mRNA in Fluid Samples

Blood samples from a subject suspected as having breast cancer or blood samples from of a subject diagnosed with cancer are drawn for analysis. The blood or blood products of the subjects are incubated with the PIP, HER2 and/or hMAM molecular beacons under conditions which allow hybridization of the molecular beacon and the PIP, HER2 and/or hMAM mRNA and the fluorescence of the samples is quantified by techniques known to those skilled in the art. It is expected that all three molecular beacons could work together in serum to detect multiple analytes at one time.

Example 8

Analysis of the Binding of the HER2 Molecular Beacon to HER2 mRNA

The HER2 molecular beacon comprising the sequence 5'-TGCCACCAGTTCAGCAGGTCCGTGGCA-3' (SEQ ID NO. 8) was chemically synthesized and modified to incorporate a TEXAS RED® fluorophore and a BLACK HOLE QUENCHER® 2 at the 5' and 3' ends, respectively.

A secondary structure construct was designed to represent the binding region of the full-length HER2 mRNA. The full-length HER2 mRNA is 4,624 bases and the secondary structure construct represents bases 2,651 through 2,724 in the full-length sequence (NCBI Accession Nos. M12036, NM_004448, and NM_001005862 in GenBank); wherein two nucleotides (GG) were added for transcriptional efficiency. The nucleotide sequence of the HER2 mRNA secondary structure construct is 5'-GGUGCCUCUUAGACCAU-GUCCGGGAAAACCGCGGACGCCUGGGCUCCCAGGAC CUGCUGAACUGGUGUAUGCAGAU-3' (SEQ ID NO. 9).

For temporal analysis of MB-mRNA hybridization, each MB sample was spiked with mRNA after establishing a fluorescence baseline. Fluorescence emission was then monitored for 30-60 minutes before the samples were heated to 95°

C. for 2 minutes and annealed at room temperature. Emission was monitored for 10 minutes after annealing.

To evaluate the in vitro MB binding to mRNA, the baseline fluorescence intensity was established, target mRNA was then added, the nucleic acids were annealed, and the fluorescence emission was monitored to establish a maximum intensity. All samples were analyzed in triplicate.

The response of the MB to target mRNA was monitored as a function of the change in fluorescence from baseline to maximum intensity. The change in fluorescence intensity was determined by averaging the baseline and maximum fluorescence values over 1 minute and calculating the difference. Values from the triplicate analysis were averaged and standard deviation was determined for error. Analysis of raw data for average fluorescence intensities and standard deviations was performed in Microsoft Excel (Redmond, Wash.) while plotting and curve fitting was performed using IGOR Pro 6 (Lake Oswego, Oreg.).

Addition of the HER2 secondary-structure mRNA construct to a sample containing HER2 MB causes an increase in fluorescence over time (FIG. 8) as a duplex forms between the molecular beacon and the mRNA.

The HER2 MB shows a HER2 mRNA dependent increase in fluorescence over a range of mRNA concentrations with a limit of detection of 3.8 nM. The MB can readily distinguish concentrations between 2.5 and 10 nM (FIG. 9). It is possible that an increase in sensitivity could be gained by increasing the concentration range over which the assay is performed from low nanomolar to mid nanomolar concentrations. If the limit on the sensitivity is the formation of MB-mRNA constructs, then increasing the concentration of mRNA in solution should allow for the formation of more MB-mRNA constructs. This would increase the reproducibility of each measurement, and therefore increase the sensitivity of the assay.

Example 9

Undiluted Serum MB Assay

The in vitro MB binding assay as in Example 8 is repeated for analysis of HER2 MB response to target HER2 mRNA in complex samples in the presence of undiluted bovine serum. All solutions are heated and annealed prior to the addition of bovine serum. Baseline fluorescence intensity is established for 1 minute and then HER2 mRNA is added. The samples are incubated in a 25° C. water bath for 3 hours at which point maximum fluorescence intensity is measured.

The response of the HER2 MB to target HER2 mRNA is monitored as a function of the change in fluorescence from baseline to maximum intensity. The change in fluorescence intensity is determined by averaging the baseline and maximum fluorescence values over 1 minute and calculating the difference. Values from the triplicate analysis are averaged and standard deviation is determined for error. Analysis of raw data for average fluorescence intensities and standard deviations is performed in Microsoft Excel (Redmond, Wash.) while plotting and curve fitting is performed using IGOR Pro 6 (Lake Oswego, Oreg.).

It is expected that the HER2 MB binds to target HER2 mRNA in complex samples in the presence of serum.

Example 10 hMAM Molecular Beacon

An hMAM molecular beacon is constructed using an appropriate donor and acceptor pair and analyzed for the specific binding of the hMAM molecular beacon to hMAM mRNA. The binding of the hMAM molecular beacon to the hMAM mRNA is evaluated in the presence or absence of serum. It is expected that the hMAM molecular beacon binds to target hMAM mRNA in complex samples in the presence of serum.

REFERENCES (1) American Cancer Society *Cancer Facts & Figures* 2011; Atlanta: American Cancer Society, 2011.
(2) Pantel, K.; Cote, R. J.; Fodstad, O. *J. Natl. Cancer Inst* 1999, 91, 1113-1124.
(3) Singletary, S. E.; Allred, C.; Ashley, P.; Bassett, L. W.; Berry, D.; Bland, K. I.; Borgen, P. I.; Clark, G.; Edge, S. B.; Hayes, D. F.; Hughes, L. L.; Hutter, R. V. P.; Morrow, M.; Page, D. L.; Recht, A.; Theriault, R. L.; Thor, A.; Weaver, D. L.; Wieand, H. S.; Greene, F. L. *J. Clin. Oncol* 2002, 20, 3628-3636.
(4) Edge, S. B.; Byrd, D. R.; Compton, C. C.; Fritz, A. G.; Greene, F. L.; Trotti, A. *AJCC Cancer Staging Manual;* 7th ed.; Springer, 2009.
(5) Singletary, S. E.; Allred, C.; Ashley, P.; Bassett, L. W.; Berry, D.; Bland, K. I.; Borgen, P. I.; Clark, G. M.; Edge, S. B.; Hayes, D. F.; Hughes, L. L.; Hutter, R. V. P.; Morrow, M.; Page, D. L.; Recht, A.; Theriault, R. L.; Thor, A.; Weaver, D. L.; Wieand, H. S.; Greene, F. L. *Surg. Clin. North Am.* 2003, 83, 803-819.
(6) Burke, H. B.; Henson, D. E. *Cancer* 1993, 72, 3131-3135.
(7) Lacroix, M. *Endocr. Relat. Cancer* 2006, 13, 1033-1067.
(8) Fleming, T. P.; Watson, M. A. *Ann. N. Y. Acad. Sci* 2000, 923, 78-89.
(9) Mitas, M.; Mikhitarian, K.; Walters, C.; Baron, P. L.; Elliott, B. M.; Brothers, T. E.; Robison, J. G.; Metcalf, J. S.; Palesch, Y. Y.; Zhang, Z.; Gillanders, W. E.; Cole, D. J. *Int. J. Cancer* 2001, 93, 162-171.
(10) Choi, D. H.; Shin, D. B.; Lee, M. H.; Lee, D. W.; Dhandapani, D.; Carter, D.; King, B. L.; Haffty, B. G. *Cancer* 2003, 98, 1587-1595.
(11) Böhm, D.; Keller, K.; Boehm, N.; Lebrecht, A.; Schmidt, M.; Kölbl, H.; Grus, F.-H. *Cancer Biology & Therapy* 2011, 12.
(12) Hassan, M. I.; Waheed, A.; Yadav, S.; Singh, T. P.; Ahmad, F. *Cell. Mol. Life Sci.* 2009, 66, 447-459.
(13) Watson, M. A.; Fleming, T. P. *Cancer Res.* 1996, 56, 860-865.
(14) Müller, V.; Witzel, I.; Lück, H. J.; Köhler, G.; von Minckwitz, G.; Möbus, V.; Sattler, D.; Wilczak, W.; Löning, T.; Jänicke, F.; Pantel, K.; Thomssen, C. *Breast Cancer Res. Treat.* 2004, 86, 9-18.
(15) Park, Y.; Kitahara, T.; Urita, T.; Yoshida, Y.; Kato, R. *World J Clin Oncol* 2011, 2, 303-310.
(16) Bagaria, S. P.; Ray, P. S.; Wang, J.; Kropcho, L.; Chung, A.; Sim, M.-S.; Shamonki, J. M.; Martino, S.; Cui, X.; Giuliano, A. E. *Annals of Surgical Oncology* 2011.
(17) Lianidou, E. S.; Markou, A. *Clin. Chem.* 2011, 57, 1242-1255.
(18) Ghossein, R. A.; Bhattacharya, S.; Rosai, J. *Clin. Cancer Res* 1999, 5, 1950-1960.
(19) Iakovlev, V. V.; Goswami, R. S.; Vecchiarelli, J.; Arneson, N. C. R.; Done, S. J. *Breast Cancer Res. Treat* 2008, 107, 145-154.
(20) Meijerink, J.; Mandigers, C.; van de Locht, L.; Tönnissen, E.; Goodsaid, F.; Raemaekers, J. *J Mol Diagn* 2001, 3, 55-61.
(21) Tyagi, S.; Kramer, F. R. *Nat. Biotechnol* 1996, 14, 303-308.

(22) Drake, T. J.; Tan, W. *Appl Spectrosc* 2004, 58, 269A-280A.
(23) Nitin, N.; Rhee, W. J.; Bao, G. *Nucleic Acids Res.* 2009, 37, 4977-4986.
(24) Tang, Z.; Liu, P.; Ma, C.; Yang, X.; Wang, K.; Tan, W.; Lv, X. *Anal. Chem.* 2011, 83, 2505-2510.
(25) Jayagopal, A.; Halfpenny, K. C.; Perez, J. W.; Wright, D. W. *J. Am. Chem. Soc.* 2010, 132, 9789-9796.
(26) Marras, S. A. E.; Tyagi, S.; Kramer, F. R. *Clin. Chim. Acta* 2006, 363, 48-60.
(27) Tsourkas, A.; Bao, G. *Brief Funct Genomic Proteomic* 2003, 1, 372-384.
(28) Goel, G.; Kumar, A.; Puniya, A. K.; Chen, W.; Singh, K. *J. Appl. Microbiol.* 2005, 99, 435-442.
(29) Benson, D. A.; Karsch-Mizrachi, I.; Lipman, D. J.; Ostell, J.; Wheeler, D. L. *Nucleic Acids Res* 2005, 33, D34-D38.
(30) Murphy, L. C.; Tsuyuki, D.; Myal, Y.; Shiu, R. P. *J. Biol. Chem* 1987, 262, 15236-15241.
(31) Zuker, M. *Nucleic Acids Res* 2003, 31, 3406-3415.
(32) Hassan, M. I.; Waheed, A.; Yadav, S.; Singh, T. P.; Ahmad, F. *Cell. Mol. Life Sci.* 2008, 66, 447-459.
(33) Tsourkas, A.; Behlke, M. A.; Bao, G. *Nucleic Acids Res* 2002, 30, 4208-4215.
(34) Mikulová V, Kološtová K, Zima T (2011) Folia Biol. (Praha) 57:151-161
(35) Königshoff M, Wilhelm J, Bohle R M, Pingoud A, Hahn M (2003) Clin. Chem. 49:219-229
(36) Grünewald K, Haun M, Fiegl M, Urbanek M, Müller-Holzner E, Massoner A, Riha K, Propst A, Marth C, Gastl G (2002) Lab. Invest. 82:1147-1153
(37) Sjödin A, Guo D, Hofer P-A, Henriksson R, Hedman H (2003) J. Invest. Dermatol. 121:428-429
(38) Königshoff M, Wilhelm J, Bohle R M, Pingoud A, Hahn M (2003) Clin Chem 49:219-229
(39) Lacroix M (2006) Endocr. Relat. Cancer 13:1033-1067
(40) Gilbey A M, Burnett D, Coleman R E, Holen I (2004) J. Clin. Pathol 57:903-911
(41) Singletary S E, Allred C, Ashley P, Bassett L W, Berry D, Bland K I, Borgen P I, Clark G, Edge S B, Hayes D F, Hughes L L, Hutter R V P, Morrow M, Page D L, Recht A, Theriault R L, Thor A, Weaver D L, Wieand H S, Greene F L (2002) J. Clin. Oncol 20:3628-3636
(42) Zieglschmid V, Hollmann C, Böcher O (2005) Crit Rev Clin Lab Sci 42:155-196
(43) Meng S, Tripathy D, Shete S, Ashfaq R, Haley B, Perkins S, Beitsch P, Khan A, Euhus D, Osborne C, Frenkel E, Hoover S, Leitch M, Clifford E, Vitetta E, Morrison L, Herlyn D, Terstappen LWMM, Fleming T, Fehm T, Tucker T, Lane N, Wang J, Uhr J (2004) PNAS 101:9393-9398
(44) Zehentner B K, Persing D H, Deme A, Toure P, Hawes S E, Brooks L, Feng Q, Hayes D C, Critichlow C W, Houghton R L, Kiviat N B (2004) Clin. Chem. 50:2069-2076
(45) Sun Y-F, Yang X-R, Zhou J, Qiu S-J, Fan J, Xu Y (2011) J. Cancer Res. Clin. Oncol. 137:1151-1173
(46) Douglas-Jones A G, Woods V (2009) Histopathology 55:107-113
(47) E. S. Kawasaki (1990) in: M. A. Innis, D. H. Gelfand, J. J. Sninsky, T. J. White (Eds.), PCR Protocols, Academic Press, San Diego, 1990, pp. 21-27
(48) Ghossein R A, Bhattacharya S, Rosai J (1999) Clin. Cancer Res 5:1950-1960
(49) Meijerink J, Mandigers C, van de Locht L, Tönnissen E, Goodsaid F, Raemaekers J (2001) J Mol Diagn 3:55-61
(50) Lakovlev V V, Goswami R S, Vecchiarelli J, Arneson N C R, Done S J (2008) Breast Cancer Res. Treat 107:145-154
(51) Wong M L, Medrano J F (2005) BioTechniques 39:75-85
(52) Combes J-D, Grelier G, Laversanne M, Voirin N, Chabaud S, Ecochard R, Lasset C, Moyret-Lalle C (2009) Anal. Biochem. 393:29-35

The invention claimed is:

1. An oligonucleotide probe consisting essentially of the sequence set forth in SEQ ID NO. 6, wherein the 5' nucleotide of the probe is labeled with at least one fluorophore and the 3' nucleotide of the probe is labeled with at least one quencher.

2. The oligonucleotide probe of claim 1, wherein the sequence set forth in SEQ ID NO. 6 exhibits a nucleotide sequence which is complementary to human prolactin inducible protein (PIP) mRNA.

3. The oligonucleotide probe of claim 1, wherein the at least one fluorophore is tetrachloro-6-carboxyfluorescein.

4. The oligonucleotide probe of claim 3, wherein the at least one quencher is a quencher having a quenching wavelength range of 480-580 nm.

5. The oligonucleotide probe of claim 1, wherein the first six nucleotides of an oligonucleotide having the sequence set forth in SEQ ID NO. 6 are complementary to the last six nucleotides of the oligonucleotide having the sequence set forth in SEQ ID NO. 6.

6. The oligonucleotide probe of claim 5, which is in a form of a stem-loop structure wherein the at least one fluorophore is in proximity to the at least one quencher whereby fluorescence of the at least one fluorophore is quenched by the at least one quencher.

7. A kit comprising the oligonucleotide probe of claim 1 and a positive control PIP mRNA consisting of the sequence set forth in SEQ ID NO. 5.

8. A method of detecting the presence of PIP mRNA in a subject having been diagnosed with cancer comprising contacting a sample comprising a bodily fluid and/or tissue biopsy from the subject with the oligonucleotide probe of claim 1 under conditions which allow hybridization of the oligonucleotide probe to the PIP mRNA in the bodily fluid and/or tissue biopsy, detecting the presence of PIP mRNA by measuring the amount of fluorescence generated by the oligonucleotide probe hybridized to the PIP mRNA, and comparing the amount of fluorescence in the sample comprising the bodily fluid and/or tissue biopsy to that of a control sample which has the oligonucleotide probe but does not comprise PIP mRNA, wherein an increase in the amount of fluorescence in the sample comprising the bodily fluid and/or tissue biopsy over the control sample indicates the presence of PIP mRNA in the bodily fluid and/or tissue biopsy.

9. The method of claim 8, wherein the oligonucleotide probe and the PIP mRNA are contacted in the presence of serum.

* * * * *

SEQUENCE LISTING

<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: PIP forward primer

<400> SEQUENCE: 1
cacattgcct tctgttttct c    21

<210> SEQ ID NO 2
<211> LENGTH: 27
<212> TYPE: DNA
<213> ORGANISM: Artificial Sequence
<220> FEATURE:
<223> OTHER INFORMATION: PIP reverse primer

<400> SEQUENCE: 2
aagcatgtta agaagtttat tttatag    27

<210> SEQ ID NO 3
<211> LENGTH: 43
<212> TYPE: DNA
<213> ORGANISM: Artificial Sequence
<220> FEATURE:
<223> OTHER INFORMATION: T7 promoter forward primer

```
<400> SEQUENCE: 3
cagtaatacg actcactata ggcacattgc cttctgtttt ctc                     43

<210> SEQ ID NO 4
<211> LENGTH: 80
<212> TYPE: RNA
<213> ORGANISM: Artificial Sequence
<220> FEATURE:
<223> OTHER INFORMATION: synthesized PIP mRNA

<400> SEQUENCE: 4
gggugacgac aauccaaaaa ccuucuacug ggacuuuuac acaacagaac ugugcaaauu   60
gcagccgucg uugauguuau                                               80

<210> SEQ ID NO 5
<211> LENGTH: 72
<212> TYPE: RNA
<213> ORGANISM: Artificial Sequence
<220> FEATURE:
<223> OTHER INFORMATION: synthesized target mRNA

<400> SEQUENCE: 5
gggugacgaa aaccuucuac ugggacuuuu acacaacaga acugugcaaa uugcagccgu   60
cguugauguu au                                                       72

<210> SEQ ID NO 6
<211> LENGTH: 27
<212> TYPE: DNA
<213> ORGANISM: Artificial Sequence
<220> FEATURE:
<223> OTHER INFORMATION: chemically synthesized molecular beacon nucleic
      acid

<400> SEQUENCE: 6
tgtgcaacga cggctgcaat ttgcaca                                       27

<210> SEQ ID NO 7
<211> LENGTH: 55
<212> TYPE: RNA
<213> ORGANISM: Artificial Sequence
<220> FEATURE:
<223> OTHER INFORMATION: synthesized non-target mRNA

<400> SEQUENCE: 7
gcgacccuga ugagcccugc gaugcagaaa ggugcugacg acacaucgaa acggu        55

<210> SEQ ID NO 8
<211> LENGTH: 27
<212> TYPE: DNA
<213> ORGANISM: Artificial Sequence
<220> FEATURE:
<223> OTHER INFORMATION: chemically synthesized molecular beacon nucleic
      acid

<400> SEQUENCE: 8
tgccaccagt tcagcaggtc cgtggca                                       27

<210> SEQ ID NO 9
<211> LENGTH: 76
<212> TYPE: RNA
<213> ORGANISM: Artificial Sequence
<220> FEATURE:
<223> OTHER INFORMATION: Synthesized HER2 mRNA

<400> SEQUENCE: 9
```

```
ggugccucuu agaccauguc cgggaaaacc gcggacgccu gggcucccag gaccugcuga      60
acugguguau gcagau                                                     76
```